United States Patent
Stadler et al.

(10) Patent No.: US 9,730,873 B2
(45) Date of Patent: Aug. 15, 2017

(54) SKIN-CARE OIL

(71) Applicant: Henkel AG & Co. KGaA, Duesseldorf (DE)

(72) Inventors: Iris Marina Stadler, Duesseldorf (DE); Marianne Waldmann-Laue, Monheim (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 15/045,361

(22) Filed: Feb. 17, 2016

(65) Prior Publication Data

US 2016/0158127 A1 Jun. 9, 2016

Related U.S. Application Data

(63) Continuation of application No. PCT/DE2014/200336, filed on Jul. 21, 2014.

(51) Int. Cl.
| | | |
|---|---|---|
| *A61K 31/21* | (2006.01) | |
| *A61K 8/37* | (2006.01) | |
| *A61K 8/34* | (2006.01) | |
| *A61Q 19/00* | (2006.01) | |
| *A61K 8/92* | (2006.01) | |

(52) U.S. Cl.
CPC ............ *A61K 8/37* (2013.01); *A61K 8/342* (2013.01); *A61K 8/375* (2013.01); *A61K 8/922* (2013.01); *A61Q 19/00* (2013.01); *A61K 2800/5922* (2013.01)

(58) Field of Classification Search
USPC ....................................................... 514/506
See application file for complete search history.

(56) References Cited

U.S. PATENT DOCUMENTS

| | | | |
|---|---|---|---|
| 6,379,681 B1 * | 4/2002 | Bordat ................. | A61K 8/06 424/400 |
| 2004/0076652 A1 | 4/2004 | Paspaleeva-Kuhn et al. | |
| 2005/0053636 A1 | 3/2005 | Von Der Fecht et al. | |
| 2009/0202461 A1 * | 8/2009 | Rodriguez ............. | A61K 8/738 424/63 |
| 2015/0038592 A1 | 2/2015 | Von Der Fecht et al. | |

FOREIGN PATENT DOCUMENTS

| | | |
|---|---|---|
| DE | 10361568 A1 | 7/2005 |
| DE | 102005003708 A1 | 8/2006 |
| EP | 1889596 A1 | 2/2008 |

OTHER PUBLICATIONS

PCT International Search Report (PCT/DE2014/200336) dated Dec. 11, 2014.

* cited by examiner

*Primary Examiner* — Rei-Tsang Shiao
(74) *Attorney, Agent, or Firm* — David K. Benson

(57) ABSTRACT

Cosmetic agents include liquid oils in a total amount of 80 to 99.5% by weight. The liquid oils include (a) at least one liquid oil with a spreadability value (25° C.) in a range of 100 mm²/10 min to less than 800 mm²/10 min, (b) at least one liquid oil with a spreadability value (25° C.) in a range of 800 mm²/10 min to less than 1050 mm²/10 min, (c) at least one liquid oil with a spreadability value (25° C.) in a range of 1050 mm²/10 min to 1800 mm²/10 min. The weight ratio of the total amount of the oils named under (a) to the sum of the respective total quantities of the oils named under (b) and (c) is in the range of 1 to 3 to 1 to 1. The cosmetic agents are suitable as skin care oils and provide a smooth skin feel and protect the skin against drying out.

10 Claims, No Drawings

SKIN-CARE OIL

FIELD OF THE INVENTION

The present invention generally relates to skin cosmetics, and more particularly relates to compositions based predominantly on liquid oil.

BACKGROUND OF THE INVENTION

Consumers are familiar with various skin care products that regenerate and care for the skin and protect it from environmental effects. Such skin care products include for this purpose active substances that have an effect on skin metabolism, for example, and thus change the skin's aesthetic appearance, and that supply the skin with fats or oils or, for example, protect it from sunlight or free radicals.

Such active substances are often provided in a cosmetic carrier, which is suitable for use on skin and supplies the skin with the cosmetic active substances. Emulsions predominantly have proven effective as potent cosmetic carriers, because they can convey both lipophilic and hydrophilic active substances. Suitable emulsions are usually oil-in-water emulsions or water-in-oil emulsions.

If lipophilic active substances predominantly are employed, skin care products in particular can be suitable that include an oil-based cosmetic carrier but are not emulsions. Such care oils should make the skin smooth and soft, nourish it intensively, and protect it from drying out. It is desirable in addition if the care oils counteract the skin aging process, regenerate the skin, and improve its structure. The elasticity of the skin and tightness of the skin should likewise be optimized.

Cosmetics with an oil base can be distributed well on the substrate, for example, the skin, but the skin absorbs the oil slowly. This results in a persistent presence of an oil film on the skin. The oil film has an unfavorable effect, inter alia, on skin haptics. The skin feels oily to sticky. It is possible, furthermore, that skin treated with the care oil comes into contact with clothing and the clothing absorbs the oil film completely or partially. The clothing is soiled in this way, on the one hand, and the effectiveness of the cosmetic on the skin is reduced, on the other.

It is therefore desirable to provide an oil-based cosmetic that can be easily distributed on a substrate, particularly the skin, and imparts a satiny and light skin feel. The cosmetic should be absorbed rapidly by the skin and provide optimal care, particularly in regard to at least one of the aforementioned care parameters.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A cosmetic agent includes, based on the total weight of the agent, liquid oils in a total amount of 80 to 99.5% by weight, (particularly of 85 to 99% by weight, particularly of 90 to 98% by weight). The agent includes as liquid oils (a) at least one liquid oil with a spreadability value (25° C.) in a range of 100 $mm^2/10$ min to less than 800 $mm^2/10$ min, (b) at least one liquid oil with a spreadability value (25° C.) in a range of 800 $mm^2/10$ min to less than 1050 $mm^2/10$ min, (c) at least one liquid oil with a spreadability value (25° C.) in a range of 1050 $mm^2/10$ min to 1800 $mm^2/10$ min, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject matter of the invention includes cosmetic agents that include, based on the total weight of the product, liquid oils in a total amount of 80 to 99.5% by weight. the agents include as liquid oils
(a) at least one liquid oil with a spreadability value (25° C.) in a range of 100 $mm^2/10$ min to less than 800 $mm^2/10$ min,
(b) at least one liquid oil with a spreadability value (25° C.) in a range of 800 $mm^2/10$ min to less than 1050 $mm^2/10$ min,
(c) at least one liquid oil with a spreadability value (25° C.) in a range of 1050 $mm^2/10$ min to 1800 $mm^2/10$ min,
with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

All data on the physical states of substances (solid, liquid, gaseous) in this application refer to standard conditions. "Standard conditions" within the meaning of the present application are a temperature of 20° C. and a pressure of 1013.25 mbar. Melting point data also refer to a pressure of 1013.25 mbar.

The composition of the invention must include one or more liquid oils in said total amount. A liquid oil according to the invention is understood to mean a liquid substance that is miscible to less than 1% by weight with double-distilled water under standard conditions.

If not explicitly defined otherwise, when ranges of numbers are given, the boundary values given in each case are included in the number range.

The term "free water" used within the context of embodiments of the invention is understood according to the invention such that the content of water of crystallization, water of hydration, or similarly molecularly bound water, which may be present in the employed ingredients, particularly in the particulate dispersed solids, does not represent free water within the meaning of the present application.

The liquid oils present in the cosmetic agent of the invention have special spreadability values. Spreading is the ability of a liquid substance after contact with a surface to spread over said surface. The spreadability value is used as a measure of the spreading behavior of a liquid substance on a surface. The spreadability value is determined as an area measured in $mm^2$ that a liquid, applied nearly as points to a horizontal surface, has after remaining for 10 minutes on this surface. Skin or a material mimicking the surface topography of skin is used as the surface within the scope of the invention. Within the meaning of the present invention, the spreadability value was measured (at an ambient temperature of 25° C. and 60% relative humidity) on a 4 cm×15 cm membrane. For this purpose, 10 μL of the substance sample was applied by means of pipette as points to a horizontal, synthetic membrane (membrane: commercial product Vitro-Skin® from the company IMS Inc (Portland, USA)). The membrane Vitro-Skin® includes protein and lipid components and has a topography, pH, critical surface tension, and an ionic strength that imitate human skin. Vitro-Skin® has a constant N-19 topography. The constant wetting properties of each Vitro-Skin® membrane simulate the skin of the human back. The spreading area on the membrane was measured after a retention time of 10 minutes. Six measurements were taken for each liquid oil. The arithmetic average of these six determinations forms the spreadability value of the invention (25° C.). If the spreadability value was measured on human skin (inner lower arm), the test proceeded mutatis mutandis but with the following deviations: To compensate for possible inhomogeneities of the substrate, the relative spreadability value was also determined versus decanoic acid tetradecyl ester as an external standard. To measure the area, a true impression of the spread lipid was taken after 10 minutes with transparent paper and the surface area was determined. The spreadability value determined for each of six test subjects was calculated using the following formula:

Area (oil to be determined on test subject)·averaged spreadability value (decanoic acid tetradecyl ester) Area (decanoic acid tetradecyl ester on test subject)

The arithmetic average of the six determinations forms the spreadability value of the invention (25° C.). The averaged spreadability value, used in the calculation, for the external standard decanoic acid tetradecyl ester was determined beforehand in 20 test subjects and the arithmetic average of the measured area was calculated.

It has emerged as preferable according to the invention, if the cosmetic agent includes as the liquid oil with a spreadability value (25° C.) in a range of 100 mm²/10 min to less than 800 mm²/10 min at least one liquid compound of the general formula (I)

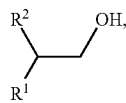

(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl). Preferably, therefore, $R^1$ stands for a $C_2$ to $C_{10}$ alkyl group, particularly octyl, and $R^2$ for a $C_4$ to $C_{12}$ alkyl group.

Liquid compounds of the formula (I) are also known as Guerbet alcohols and can be obtained as the product of the so-called Guerbet reaction. It is preferred according to the invention to use octyldodecanol ($R^1$=$C_8$ alkyl and $R^2$=$C_{10}$ alkyl) as a liquid compound according to the formula (I).

It has emerged as preferable according to the invention, if the cosmetic agent includes as the liquid oil with a spreadability value (25° C.) in a range of 100 mm²/10 min to less than 800 mm²/10 min at least one liquid compound of the general formula (II)

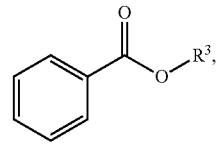

(II)

where $R^3$ stands for a $C_{10}$ to $C_{16}$ hydrocarbon group, particularly a $C_{12}$ to $C_{15}$ hydrocarbon group. Preferably $R^3$ stands for a $C_{10}$ to $C_{16}$ alkyl group, particularly a $C_{12}$ to $C_{15}$ alkyl group.

Preferred liquid oils according to the formula (II) are selected from benzoic acid esters of linear or branched $C_{10-16}$ alkanols. Especially preferred are benzoic acid-$C_{12}$-$C_{15}$-alkyl esters, e.g., obtainable as the commercial product Finsolv® TN, and benzoic acid isostearyl ester, e.g., obtainable as the commercial product Finsolv® SB.

Within the scope of an especially preferred embodiment of the invention, the cosmetic agent includes as the liquid oil with a spreadability value (25° C.) in a range of 100 mm²/10 min to less than 800 mm²/10 min at least one liquid compound of the general formula (I) (see above) together with at least one compound of the general formula (II) (see above). The preferred embodiments of the compounds of the formulas (I) and (II) are also preferred for this embodiment.

The addition of at least one natural oil (such as, e.g., almond oil, amaranth oil, Manila oil, macadamia nut oil, argan oil) as the liquid oil with a spreadability value (25° C.) in a range of 100 mm²/10 min to less than 800 mm²/10 min is also novel.

Liquid oils with a spreadability value (25° C.) of less than 100 mm²/10 min should not be used if possible or be used in the smallest amounts in the cosmetic agents of the invention. It is preferred, therefore, to use such liquid oils in amounts of 0 to 0.25% by weight, particularly 0 to 0.05% by weight.

It has emerged as preferable according to the invention, if the cosmetic agent includes as the liquid oil with a spreadability value (25° C.) in a range of 800 mm²/10 min to less than 1050 mm²/10 min at least one compound of the general formula (III)

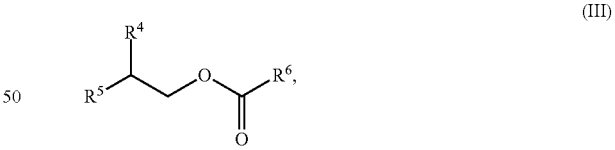

(III)

where $R^4$ stands for an alkyl group having 2 to 4 carbon atoms, particularly for ethyl,
$R^5$ stands for an alkyl group having 4 to 6 carbon atoms,
$R^6$ stands for an alkyl group having 7 to 17 carbon atoms.

It is especially preferably according to the invention to select the liquid oils according to the formula (III) from at least one compound in which $R^4$ stands for an ethyl group, $R^5$ for an n-butyl group, and $R^6$ for an alkyl group having 7 to 15 carbon atoms (particularly for an alkyl group having 11 to 15 carbon atoms).

Preferred compounds of the formula (III) are selected from 2-ethylhexyl palmitate, 2-ethylhexyl stearate, 2-ethylhexyl myristate, or mixtures thereof 2-Ethylhexyl palmitate is very especially preferred.

It has emerged as preferable according to the invention, if the cosmetic agent includes as the liquid oil with a spreadability value (25° C.) in a range of 800 mm$^2$/10 min to less than 1050 mm$^2$/10 min at least one ester of isopropanol with a $C_{16}$ to $C_{20}$ fatty acid.

Preferred compounds of the esters of isopropanol with a $C_{16}$ to $C_{20}$ fatty acid are selected from isopropyl stearate, isopropyl palmitate, isopropyl myristate, and mixtures thereof. Very especially preferred is isopropyl stearate.

Within the scope of an especially preferred embodiment of the invention, the cosmetic agent includes as the liquid oil with a spreadability value (25° C.) in a range of 800 mm$^2$/10 min to less than 1050 mm$^2$/10 min at least one liquid compound of the general formula (III) (see above) together with at least one ester of isopropanol with a $C_{16}$ to $C_{20}$ fatty acid. The preferred embodiments of the compounds of the formulas (III) and of the ester of isopropanol with a $C_{16}$ to $C_{20}$ fatty acid (see above) likewise apply as preferred to this embodiment.

It has emerged as preferable according to the invention, if the cosmetic agent includes as the liquid oil with a spreadability value (25° C.) in a range of 1050 mm$^2$/10 min to 1800 mm$^2$/10 min at least one compound of the general formula (IV)

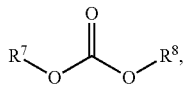

(IV)

where $R^7$ and $R^8$ independently of one another stand for a linear or branched alkyl group having 6 to 10 carbon atoms, particularly for a linear or branched alkyl group having 8 carbon atoms.

Preferred compounds according to the formula (IV) are selected from dicaprylyl carbonate (dioctyl carbonate), di(2-ethylhexyl) carbonates, or mixtures thereof. Very especially preferred is dicaprylyl carbonate, which can be obtained, for example, with the trade name Cetiol CC® from the company BASF SE.

It has emerged as preferable according to the invention, if the cosmetic agent includes as the liquid oil with a spreadability value (25° C.) in a range of 1050 mm$^2$/10 min to 1800 mm$^2$/10 min at least one ester of a ($C_4$ to $C_6$) alkanol with a $C_{16}$ to $C_{20}$ fatty acid. n-Butanol, n-hexanol, tert-butanol, sec-butanol, or n-pentanol is suitable as preferred suitable ($C_4$ to $C_6$) alkanols. N-Hexanol is especially preferred. An especially preferred ester is hexyl laurate.

Within the scope of an especially preferred embodiment of the invention, the cosmetic agent of the invention includes as the liquid oil with a spreadability value (25° C.) in a range of 1050 mm$^2$/10 min to 1800 mm$^2$/10 min at least one liquid compound of the general formula (IV) (see above) together with at least one ester of a ($C_4$ to $C_6$) alkanol with a $C_{16}$ to $C_{20}$ fatty acid. N-Butanol, n-hexanol, tert-butanol, sec-butanol, or n-pentanol is suitable as preferred suitable ($C_4$ to $C_6$) alkanols. Especially preferred is n-Hexanol. An especially preferred ester is hexyl laurate.

It is preferred according to the invention, if the cosmetic agent of the invention, based on the total weight of the composition, includes the liquid oil in a total amount of 85 to 99% by weight, particularly of 90 to 98% by weight.

It is naturally to be noted within the scope of the following quantitative data and is mentioned mostly by way of precaution that both the indication of the above total amount of liquid oil and the stipulation of all weight ratios of the various spreading oils (a), (b), and (c) have a mutual limiting effect on the (preferred) weight amounts to be used of the particular oils.

Within the scope of other embodiments, it proved to be advantageous, if the cosmetic agents of the invention include a liquid oil with a spreadability value (25° C.) in a range of 100 mm$^2$/10 min to less than 800 mm$^2$/10 min in a total amount of 32 to 42% by weight.

Within the scope of other embodiments, it proved to be advantageous, if the cosmetic agents of the invention include a liquid oil with a spreadability value (25° C.) in a range of 800 mm$^2$/10 min to less than 1050 mm$^2$/10 min in a total amount of 35 to 50% by weight. Said preferred total amount is preferably combined together with the preferred total amount of the liquid oil with a spreadability value (25° C.) in a range of 100 mm$^2$/10 min to less than 800 mm$^2$/10 min (see above).

Within the scope of other embodiments, it proved to be advantageous, if the cosmetic agents of the invention include a liquid oil with a spreadability value (25° C.) in a range of 1050 mm$^2$/10 min to 1800 mm$^2$/10 min in a total amount of 12 to 22% by weight. Said preferred total amount is preferably combined together with the preferred total amount of the liquid oil with a spreadability value (25° C.) in a range of 100 mm$^2$/10 min to less than 800 mm$^2$/10 min (see above).

Within the scope of an especially preferred embodiment, it proved to be advantageous, if the cosmetic agents of the invention each include, based on the total weight of the cosmetic agent, (a) a liquid oil with a spreadability value (25° C.) in a range of 100 mm$^2$/10 min to less than 800 mm$^2$/10 min in a total amount of 32 to 42% by weight, (b) a liquid oil with a spreadability value (25° C.) in a range of 800 mm$^2$/10 min to less than 1050 mm$^2$/10 min in a total amount of 35 to 50% by weight, (c) a liquid oil with a spreadability value (25° C.) in a range of 1050 mm$^2$/10 min to 1800 mm$^2$/10 min in a total amount of 12 to 22% by weight.

Within the scope of other embodiments, it proved to be advantageous, if the total amount of the oils named under (b) relative to the sum of the respective total amounts of the oils named under (a) and (c) is in the range of 1.5 to 1 to 1 to 2, particularly preferably between 1.2 to 1 and 1 to 1.8, and very particularly preferably between 1 to 1.2 to 1 to 1.7. Said preferred embodiment can be combined in turn preferably with one or more of the aforementioned preferred total amounts of said liquid oils.

The cosmetic compositions of the invention are preferably low in water to anhydrous; in particular they are anhydrous. It has proven to be preferable, if the cosmetic compositions of the invention include free water in an amount of 0 to 0.1% by weight, particularly preferably of 0 to 0.05% by weight, very particularly preferably of 0 to 0.01% by weight, and most preferably of 0 to 0.001% by weight, based in each case on the total weight of the cosmetic agent.

Cosmetic agents preferred according to the invention are transparent. A cosmetic agent is regarded as transparent, if a letter "A" (Times New Roman font size of 10 points) located 10 cm away from the sample is recognized with the naked eye through a sample of the cosmetic agent with a layer thickness d of 3 cm.

Especially Preferred Embodiments

Examples of the invention are characterized by the embodiments (A) to (P):

(A): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils
- (a) at least one liquid oil with a spreadability value (25° C.) in a range of 100 mm$^2$/10 min to less than 800 mm$^2$/10 min, selected from one or more compounds according to the formula (I)

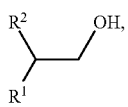

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl),
- (b) at least one liquid oil with a spreadability value (25° C.) in a range of 800 mm$^2$/10 min to less than 1050 mm$^2$/10 min,
- (c) at least one liquid oil with a spreadability value (25° C.) in a range of 1050 mm$^2$/10 min to 1800 mm$^2$/10 min, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(B): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils
- (a) at least two liquid oils with a spreadability value (25° C.) in a range of 100 mm$^2$/10 min to less than 800 mm$^2$/10 min, whereby at least one of these oils is selected from one or more compounds according to the formula (I)

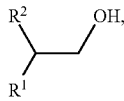

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and whereby at least one other of these oils is selected from one or more compounds of the formula (II)

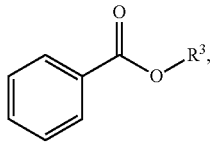

where $R^3$ stands for a $C_{10}$ to $C_{16}$ hydrocarbon group, particularly a $C_{12}$ to $C_{15}$ hydrocarbon group,
- (b) at least one liquid oil with a spreadability value (25° C.) in a range of 800 mm$^2$/10 min to less than 1050 mm$^2$/10 min,
- (c) at least one liquid oil with a spreadability value (25° C.) in a range of 1050 mm$^2$/10 min to 1800 mm$^2$/10 min, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(C): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils
- (a) at least two liquid oils with a spreadability value (25° C.) in a range of 100 mm$^2$/10 min to less than 800 mm$^2$/10 min, whereby at least one of these oils is selected from one or more compounds according to the formula (I)

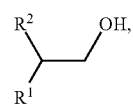

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and whereby at least one other of these oils is selected from one or more compounds of the formula (II)

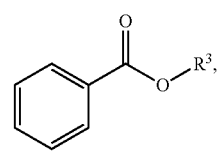

where $R^3$ stands for a $C_{10}$ to $C_{16}$ hydrocarbon group, particularly $C_{12}$ to $C_{15}$ hydrocarbon group,
- (b) at least one liquid oil with a spreadability value (25° C.) in a range of 800 mm$^2$/10 min to less than 1050 mm$^2$/10 min, selected from at least one compound of the formula (III)

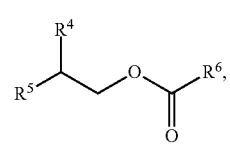

where $R^4$ stands for an alkyl group having 2 to 4 carbon atoms, particularly for ethyl, $R^5$ stands for an alkyl group having 4 to 6 carbon atoms, $R^6$ stands for an alkyl group having 7 to 17 carbon atoms, (c) at least one liquid oil with a spreadability value (25° C.) in a range of 1050 mm²/10 min to 1800 mm²/10 min, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(D): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils (a) at least two liquid oils with a spreadability value (25° C.) in a range of 100 mm²/10 min to less than 800 mm²/10 min, whereby at least one of these oils is selected from one or more compounds according to the formula (I)

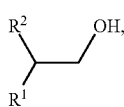

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and whereby at least one other of these oils is selected from one or more compounds of the formula (II)

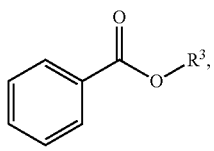

where $R^3$ stands for a $C_{10}$ to $C_{16}$ hydrocarbon group, particularly $C_{12}$ to $C_{15}$ hydrocarbon group, (b) at least two liquid oils with a spreadability value (25° C.) in a range of 800 mm²/10 min to less than 1050 mm²/10 min, whereby at least one of these oils is selected from at least one compound of the formula (III)

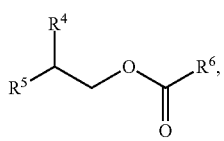

where $R^4$ stands for an alkyl group having 2 to 4 carbon atoms, particularly for ethyl, $R^5$ stands for an alkyl group having 4 to 6 carbon atoms, $R^6$ stands for an alkyl group having 7 to 17 carbon atoms, and whereby at least one other of these oils is selected from at least one ester of isopropanol with a $C_{16}$ to $C_{20}$ fatty acid, (c) at least one liquid oil with a spreadability value (25° C.) in a range of 1050 mm²/10 min to 1800 mm²/10 min, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(E): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils (a) at least two liquid oils with a spreadability value (25° C.) in a range of 100 mm²/10 min to less than 800 mm²/10 min, whereby at least one of these oils is selected from one or more compounds according to the formula (I)

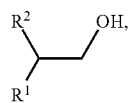

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and whereby at least one other of these oils is selected from one or more compounds of the formula (II)

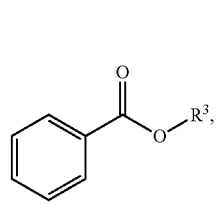

where $R^3$ stands for a $C_{10}$ to $C_{16}$ hydrocarbon group, particularly a $C_{12}$ to $C_{15}$ hydrocarbon group, (b) at least two liquid oils with a spreadability value (25° C.) in a range of 800 mm²/10 min to less than 1050 mm²/10 min, whereby at least one of these oils is selected from at least one compound of the formula (III)

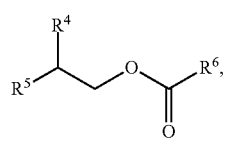

where $R^4$ stands for an alkyl group having 2 to 4 carbon atoms, particularly for ethyl, $R^5$ stands for an alkyl group having 4 to 6 carbon atoms, $R^6$ stands for an alkyl group having 7 to 17 carbon atoms,
and
whereby at least one other of these oils is selected from at least one ester of isopropanol with a $C_{16}$ to $C_{20}$ fatty acid, (c) at least one liquid oil with a spreadability value (25° C.) in a range of 1050 mm$^2$/10 min to 1800 mm$^2$/10 min, selected from at least one compound of the formula (IV)

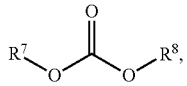
(IV)

where $R^7$ and $R^8$ independently of one another stand for a linear or branched alkyl group having 6 to 10 carbon atoms, particularly for a linear or branched alkyl group having 8 carbon atoms,
with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(F): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils (a) at least two liquid oils with a spreadability value (25° C.) in a range of 100 mm$^2$/10 min to less than 800 mm$^2$/10 min, whereby at least one of these oils is selected from one or more compounds according to the formula (I)

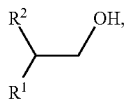
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl),
and
whereby at least one other of these oils is selected from one or more compounds of the formula (II)

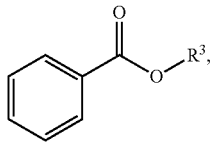
(II)

where $R^3$ stands for a $C_{10}$ to $C_{16}$ hydrocarbon group, particularly a $C_{12}$ to $C_{15}$ hydrocarbon group, (b) at least one liquid oil with a spreadability value (25° C.) in a range of 800 mm$^2$/10 min to less than 1050 mm$^2$/10 min, (c) at least one liquid oil with a spreadability value (25° C.) in a range of 1050 mm$^2$/10 min to 1800 mm$^2$/10 min, selected from at least one compound of the formula (IV)

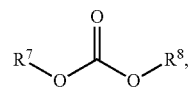
(IV)

where $R^7$ and $R^8$ independently of one another stand for a linear or branched alkyl group having 6 to 10 carbon atoms, particularly for a linear or branched alkyl group having 8 carbon atoms,
with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(G): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils (a) at least one liquid oil with a spreadability value (25° C.) in a range of 100 mm$^2$/10 min to less than 800 mm$^2$/10 min, selected from one or more compounds according to the formula (I)

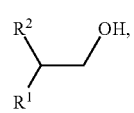
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), (b) at least one liquid oil with a spreadability value (25° C.) in a range of 800 mm$^2$/10 min to less than 1050 mm$^2$/10 min, (c) at least one liquid oil with a spreadability value (25° C.) in a range of 1050 mm$^2$/10 min to 1800 mm$^2$/10 min, selected from at least one compound of the formula (IV)

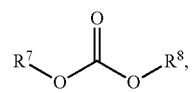
(IV)

where $R^7$ and $R^8$ independently of one another stand for a linear or branched alkyl group having 6 to 10 carbon atoms, particularly for a linear or branched alkyl group having 8 carbon atoms,
with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(H): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils (a) at least two liquid oils with a spreadability value (25° C.) in a range of 100 mm²/10 min to less than 800 mm²/10 min, whereby at least one of these oils is selected from one or more compounds according to the formula (I)

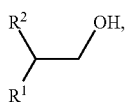
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and whereby at least one other of these oils is selected from one or more compounds of the formula (II)

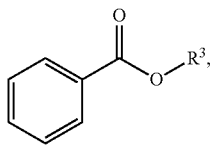
(II)

where $R^3$ stands for a $C_{10}$ to $C_{16}$ hydrocarbon group, particularly a $C_{12}$ to $C_{15}$ hydrocarbon group, (b) at least two liquid oils with a spreadability value (25° C.) in a range of 800 mm²/10 min to less than 1050 mm²/10 min, whereby at least one of these oils is selected from at least one compound of the formula (III)

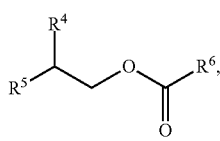
(III)

where $R^4$ stands for an alkyl group having 2 to 4 carbon atoms, particularly for ethyl, $R^5$ stands for an alkyl group having 4 to 6 carbon atoms, $R^6$ stands for an alkyl group having 7 to 17 carbon atoms, and whereby at least one other of these oils is selected from at least one ester of isopropanol with a $C_{16}$ to $C_{20}$ fatty acid, (c) at least two liquid oils with a spreadability value (25° C.) in a range of 1050 mm²/10 min to 1800 mm²/10 min, whereby at least one of these oils is selected from at least one compound of the formula (IV)

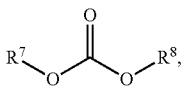
(IV)

where $R^7$ and $R^8$ independently of one another stand for a linear or branched alkyl group having 6 to 10 carbon atoms, particularly for a linear or branched alkyl group having 8 carbon atoms, and whereby at least one other of these oils is selected from at least one ester of a ($C_4$ to $C_6$) alkanol with a $C_{16}$ to $C_{20}$ fatty acids, particularly hexyl laurate, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

In particular, the preferred weight amounts in each case as the total amount of the liquid oils under (a), (b), and (c) are considered to be preferable mutatis mutandis for the embodiments (A) to (H).

(I): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils at least (a) in a total amount of 32 to 42% by weight of a liquid oil with a spreadability value (25° C.) in a range of 100 mm²/10 min to less than 800 mm²/10 min, selected from one or more compounds according to the formula (I)

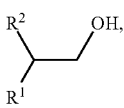
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), (b) at least one liquid oil with a spreadability value (25° C.) in a range of 800 mm²/10 min to less than 1050 mm²/10 min, (c) at least one liquid oil with a spreadability value (25° C.) in a range of 1050 mm²/10 min to 1800 mm²/10 min, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(J): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils at least (a) in a total amount of 32 to 42% by weight of a liquid oil with a spreadability value (25° C.) in a range of 100 mm²/10 min to less than 800 mm²/10 min, whereby this is a mixture of one or more compounds according to the formula (I)

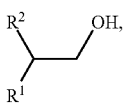
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and
one or more compounds of the formula (II)

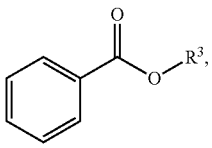
(II)

where $R^3$ stands for a $C_{10}$ to $C_{16}$ hydrocarbon group, particularly a $C_{12}$ to $C_{15}$ hydrocarbon group,
(b) at least one liquid oil with a spreadability value (25° C.) in a range of 800 mm²/10 min to less than 1050 mm²/10 min,
(c) at least one liquid oil with a spreadability value (25° C.) in a range of 1050 mm²/10 min to 1800 mm²/10 min,
with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(K): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils at least
(a) in a total amount of 32 to 42% by weight of a liquid oil with a spreadability value (25° C.) in a range of 100 mm²/10 min to less than 800 mm²/10 min, whereby this is a mixture of one or more compounds according to the formula (I)

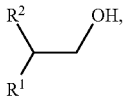
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and
one or more compounds of the formula (II)

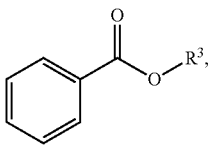
(II)

where $R^3$ stands for a $C_{10}$ to $C_{16}$ hydrocarbon group, particularly a $C_{12}$ to $C_{15}$ hydrocarbon group,
(b) in a total amount of 35 to 50% by weight of a liquid oil with a spreadability value (25° C.) in a range of 800 mm²/10 min to less than 1050 mm²/10 min, selected from one or more compounds of the formula (III)

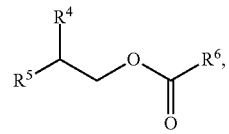
(III)

where $R^4$ stands for an alkyl group having 2 to 4 carbon atoms, particularly for ethyl,
$R^5$ stands for an alkyl group having 4 to 6 carbon atoms,
$R^6$ stands for an alkyl group having 7 to 17 carbon atoms,
(c) at least one liquid oil with a spreadability value (25° C.) in a range of 1050 mm²/10 min to 1800 mm²/10 min,
with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(L): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils
(a) in a total amount of 32 to 42% by weight of a liquid oil with a spreadability value (25° C.) in a range of 100 mm²/10 min to less than 800 mm²/10 min, whereby this is a mixture of one or more compounds according to the formula (I)

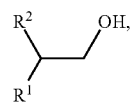
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and
one or more compounds of the formula (II)

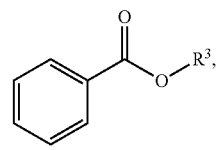
(II)

where $R^3$ stands for a $C_{10}$ to $C_{16}$ hydrocarbon group, particularly a $C_{12}$ to $C_{15}$ hydrocarbon group,
(b) in a total amount of 35 to 50% by weight of a liquid oil with a spreadability value (25° C.) in a range of 800 mm$^2$/10 min to less than 1050 mm$^2$/10 min, whereby this is a mixture of one or more compounds of the formula (III)

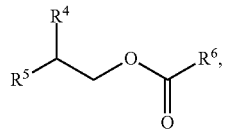

(III)

where R$^4$ stands for an alkyl group having 2 to 4 carbon atoms, particularly for ethyl,
R$^5$ stands for an alkyl group having 4 to 6 carbon atoms,
R$^6$ stands for an alkyl group having 7 to 17 carbon atoms,
and selected from at least one ester of isopropanol with a C$_{16}$ to C$_{20}$ fatty acid, (c) at least one liquid oil with a spreadability value (25° C.) in a range of 1050 mm$^2$/10 min to 1800 mm$^2$/10 min,
with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(M): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils at least (a) in a total amount of 32 to 42% by weight of a liquid oil with a spreadability value (25° C.) in a range of 100 mm$^2$/10 min to less than 800 mm$^2$/10 min, whereby this is a mixture of one or more compounds according to the formula (I)

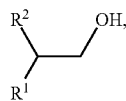

(I)

where R$^1$ stands for a C$_2$ to C$_{10}$ hydrocarbon group (preferably alkyl), particularly octyl, and R$^2$ for a C$_4$ to C$_{12}$ hydrocarbon group (preferably alkyl), and
one or more compounds of the formula (II)

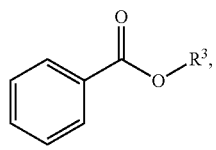

(II)

where R$^3$ stands for a C$_{10}$ to C$_{16}$ hydrocarbon group, particularly a C$_{12}$ to C$_{15}$ hydrocarbon group, (b) in a total amount of 35 to 50% by weight of a liquid oil with a spreadability value (25° C.) in a range of 800 mm$^2$/10 min to less than 1050 mm$^2$/10 min, whereby this is a mixture of one or more compounds of the formula (III)

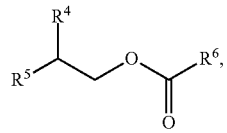

(III)

where R$^4$ stands for an alkyl group having 2 to 4 carbon atoms, particularly for ethyl,
R$^5$ stands for an alkyl group having 4 to 6 carbon atoms,
R$^6$ stands for an alkyl group having 7 to 17 carbon atoms,
and selected from at least one ester of isopropanol with a C$_{16}$ to C$_{20}$ fatty acid, (c) in a total amount of 12 to 22% by weight of a liquid oil with a spreadability value (25° C.) in a range of 1050 mm$^2$/10 min to 1800 mm$^2$/10 min, selected from at least one compound of the formula (IV)

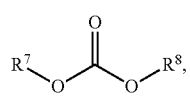

(IV)

where R$^7$ and R$^8$ independently of one another stand for a linear or branched alkyl group having 6 to 10 carbon atoms, particularly for a linear or branched alkyl group having 8 carbon atoms, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(N): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils at least (a) in a total amount of 32 to 42% by weight of a liquid oil with a spreadability value (25° C.) in a range of 100 mm$^2$/10 min to less than 800 mm$^2$/10 min, whereby this is a mixture of one or more compounds according to the formula (I)

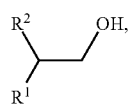

(I)

where R$^1$ stands for a C$_2$ to C$_{10}$ hydrocarbon group (preferably alkyl), particularly octyl, and R$^2$ for a C$_4$ to C$_{12}$ hydrocarbon group (preferably alkyl), and
one or more compounds of the formula (II)

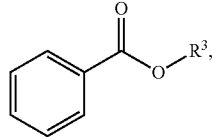
(II)

where $R^3$ stands for a $C_{10}$ to $C_{16}$ hydrocarbon group, particularly a $C_{12}$ to $C_{15}$ hydrocarbon group, (b) in a total amount of 35 to 50% by weight of a liquid oil with a spreadability value (25° C.) in a range of 800 mm²/10 min to less than 1050 mm²/10 min, whereby this is a mixture of one or more compounds of the formula (III)

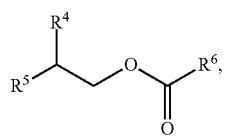
(III)

where $R^4$ stands for an alkyl group having 2 to 4 carbon atoms, particularly for ethyl, $R^5$ stands for an alkyl group having 4 to 6 carbon atoms, $R^6$ stands for an alkyl group having 7 to 17 carbon atoms, with at least one ester of isopropanol with a $C_{16}$ to $C_{20}$ fatty acid, (c) in a total amount of 12 to 22% by weight of a liquid oil with a spreadability value (25° C.) in a range of 1050 mm²/10 min to 1800 mm²/10 min, whereby this is a mixture of at least one compound of the formula (IV)

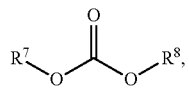
(IV)

where $R^7$ and $R^8$ independently of one another stand for a linear or branched alkyl group having 6 to 10 carbon atoms, particularly for a linear or branched alkyl group having 8 carbon atoms, with at least one ester of a ($C_4$ to $C_6$) alkanol with a $C_{16}$ to $C_{20}$ fatty acids, particularly hexyl laurate, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(O): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils (a) in a total amount of 32 to 42% by weight of a liquid oil with a spreadability value (25° C.) in a range of 100 mm²/10 min to less than 800 mm²/10 min, whereby this is a mixture of one or more compounds according to the formula (I)

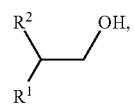
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), and
one or more compounds of the formula (II)

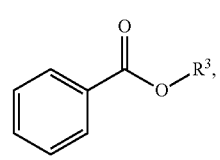
(II)

where $R^3$ stands for a $C_{10}$ to $C_{16}$ hydrocarbon group, particularly a $C_{12}$ to $C_{15}$ hydrocarbon group, (b) at least one liquid oil with a spreadability value (25° C.) in a range of 800 mm²/10 min to less than 1050 mm²/10 min, (c) in a total amount of 12 to 22% by weight of a liquid oil with a spreadability value (25° C.) in a range of 1050 mm²/10 min to 1800 mm²/10 min, selected from at least one compound of the formula (IV)

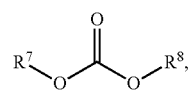
(IV)

where $R^7$ and $R^8$ independently of one another stand for a linear or branched alkyl group having 6 to 10 carbon atoms, particularly for a linear or branched alkyl group having 8 carbon atoms, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

(P): A cosmetic agent, including, based in each case on the total weight of the agent, liquid oils in a total amount of 80 to 99.5% by weight, (particularly of 85 to 99% by weight, particularly of 90 to 98% by weight), characterized in that it includes as liquid oils (a) in a total amount of 32 to 42% by weight of a liquid oil with a spreadability value (25° C.) in a range of 100 mm²/10 min to less than 800 mm²/10 min, selected from one or more compounds according to the formula (I)

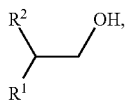
(I)

where $R^1$ stands for a $C_2$ to $C_{10}$ hydrocarbon group (preferably alkyl), particularly octyl, and $R^2$ for a $C_4$ to $C_{12}$ hydrocarbon group (preferably alkyl), (b) at least one liquid oil with a spreadability value (25° C.) in a range of 800 mm²/10 min to less than 1050 mm²/10 min, (c) in a total amount of 12 to 22% by weight of a liquid oil with a spreadability value (25° C.) in a range of 1050 mm²/10 min to 1800 mm²/10 min, selected from at least one compound of the formula (IV)

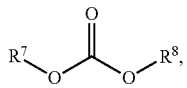
(IV)

where $R^7$ and $R^8$ independently of one another stand for a linear or branched alkyl group having 6 to 10 carbon atoms, particularly for a linear or branched alkyl group having 8 carbon atoms, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

In particular, the preferred compounds of the specific liquid oils (a), (b), and (c) are considered to be preferable mutatis mutandis for the embodiment (A) to (P). Further, the features of the invention previously described in general as preferred embodiments are also considered to be preferable for the embodiments (A) to (P).

Cosmetic agents preferred according to the invention include in addition at least one fatty acid ester of at least one linear or branched $C_6$ to $C_{18}$ fatty acid with ascorbic acid. It is particularly preferred in turn, if the fatty acid ester of at least one linear or branched $C_6$ to $C_{18}$ fatty acid with ascorbic acid is selected from one or more compounds of ascorbyl tetraisopalmitate (also ascorbyl tetrakis(2-hexyl decanoate)) and ascorbyl palmitate (INCI name: Ascorbyl Palmitate).

Cosmetic agents preferred according to the invention include in addition at least one carotenoid.

Carotenoids suitable according to the invention include carotenes (exclusively hydrocarbons) and xanthophylls (oxygen-containing carotenes), whose basic framework consists of eight isoprene units. Especially suitable carotenoids of the invention are selected from lutein, α-carotene, β-carotene, and lycopene. β-Carotene is very particularly preferred.

Agents preferred according to the invention include in addition at least one 6,7-disubstituted 2,2-dialkyl chroman or chromene of the general formula (CI) or (CII)

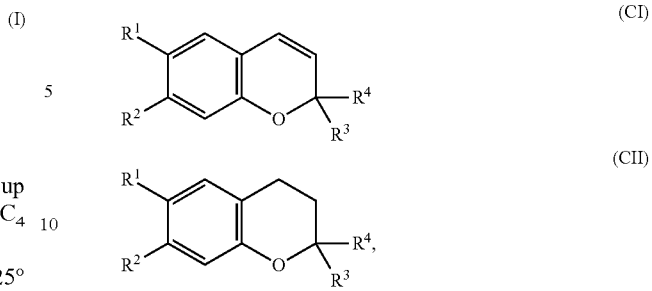

where $R^1$ and $R^2$ independently of one another represent an OH group, a methoxy group, or a $CF_3CH_2O$ group and $R^3$ and $R^4$ independently of one another a ($C_1$ to $C_4$) alkyl group.

The substituents $R^1$ and $R^2$ according to formulas (CI) and (CII) are independently of one another selected from an OH group, a methoxy group, and a $CF_3CH_2O$ group. In a preferred embodiment, $R^1$ and $R^2$ according to formulas (CI) and (CII) are selected independently of one another from an OH group and a methoxy group. In a particularly preferred embodiment, according to formulas (CI) and (CII) $R^1$ represents an OH group and $R^2$ a methoxy group.

The substituents $R^3$ and $R^4$ according to formulas (CI) and (CII) represent independently of one another a ($C_1$ to $C_4$) alkyl group. A ($C_1$ to $C_4$) alkyl group according to the invention is understood to mean a methyl, ethyl, n-propyl, isopropyl, n-butyl, isobutyl or 2-methylpropyl, sec-butyl or 1-methylpropyl, or a tert-butyl group. In a preferred embodiment, $R^3$ and $R^4$ according to formulas (CI) and (CII) are selected independently of one another from a methyl, ethyl, n-propyl, isopropyl, and an n-butyl group. Particularly preferably, $R^3$ and $R^4$ according to formulas (CI) and (CII) independently of one another represent a methyl or ethyl group. It is exceptionally preferred that $R^3$ and $R^4$ are identical.

Particularly preferred according to the invention are 6,7-disubstituted 2,2-dialkyl chromans. An active substance used exceptionally preferably according to the invention is 2,2-dimethyl-6-hydroxy-7-methoxychroman with the systematic name 3,4-dihydro-6-methoxy-2,2-dimethyl-2H-1-benzopyran-6-ol and the INCI name Dimethylmethoxy Chromanol. The substance can be obtained under the trade name Lipochroman-6 from the company Lipotec S.A.

The 6,7-disubstituted 2,2-dialkylchromans or chromenes of the general formulas (CI) or (CII) are used according to the invention preferably in amounts of 0.001 to 0.2% by weight, preferably 0.005 to 0.1% by weight, based in each case on the total weight of the agent.

A second subject matter of the invention is the use of a cosmetic agent of the first subject matter of the invention as a skin cosmetic.

It is preferred in turn within the scope of this subject matter of the invention to use the novel cosmetic agents of the first subject matter of the invention as a skin cosmetic for caring for and/or protecting the skin from drying out.

Further, all preferred embodiments of the parameters for the novel agents of the first subject matter of the invention are also preferred mutatis mutandis for the second subject matter of the invention.

A third subject matter of the invention is a method in which a cosmetic agent of the first subject matter of the invention is applied to the skin and is left on it, particularly for at least one hour.

Further, all preferred embodiments of the parameters of the novel agent of the first subject matter of the invention are also preferred mutatis mutandis for the third subject matter of the invention.

Very especially preferred embodiments of the invention are characterized by the following points:

First, a cosmetic agent includes, based on the total weight of the agent, liquid oils in a total amount of 80 to 99.5% by weight, (particularly of 85 to 99% by weight, particularly of 90 to 98% by weight), wherein the agent includes as liquid oils (a) at least one liquid oil with a spreadability value (25° C.) in a range of 100 mm²/10 min to less than 800 mm²/10 min,
(b) at least one liquid oil with a spreadability value (25° C.) in a range of 800 mm²/10 min to less than 1050 mm²/10 min,
(c) at least one liquid oil with a spreadability value (25° C.) in a range of 1050 mm²/10 min to 1800 mm²/10 min, with the proviso that the weight ratio of the total amount of the oils named under (a) to the sum of the respective total amounts of the oils named under (b) and (c) is in the range of 1 to 3 to 1 to 1, preferably of 1 to 2.5 to 1 to 1.2, particularly preferably of 1 to 2 to 1 to 1.3, and very particularly preferably of 1 to 1.9 to 1 to 1.4.

The cosmetic agent may include as a liquid oil with a spreadability value (25° C.) in a range of 100 mm²/10 min to less than 800 mm²/10 min, at least one liquid compound of the general formula (I)

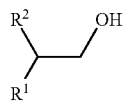

(I)

where $R^1$ stands for a $C_2$ to $C_{10}$ hydrocarbon group, particularly octyl, and $R^2$ for a $C_4$ to $C_{12}$ hydrocarbon group.

The cosmetic agent may include as a liquid oil with a spreadability value (25° C.) in a range of 100 mm²/10 min to less than 800 mm²/10 min at least one liquid compound of the general formula (II)

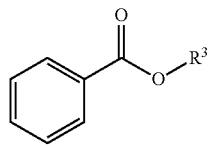

(II)

where $R^3$ stands for a $C_{10}$ to $C_{16}$ hydrocarbon group, particularly a $C_{12}$ to $C_{15}$ hydrocarbon group.

The cosmetic agent may include as a liquid oil with a spreadability value (25° C.) in a range of 800 mm²/10 min to less than 1050 mm²/10 min at least one compound of the general formula (III)

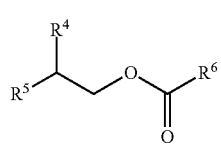

(III)

where $R^4$ stands for an alkyl group having 2 to 4 carbon atoms, particularly for ethyl, $R^5$ stands for an alkyl group having 4 to 6 carbon atoms, and $R^6$ stands for an alkyl group having 7 to 17 carbon atoms.

The cosmetic agent may include as a liquid oil with a spreadability value (25° C.) in a range of 800 mm²/10 min to less than 105 mm²/10 min at least one ester of isopropanol with a $C_{16}$ to $C_{20}$ fatty acid.

The cosmetic agent may include as a liquid oil with a spreadability value (25° C.) in a range of 1050 mm²/10 min to 1800 mm²/10 min at least one compound of the formula (IV)

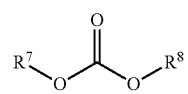

(IV)

where $R^7$ and $R^8$ independently of one another stand for a linear or branched alkyl group having 6 to 10 carbon atoms, particularly for a linear or branched alkyl group having 8 carbon atoms.

The cosmetic agent may include as a liquid oil with a spreadability value (25° C.) in a range of 1050 mm²/10 min to 1800 mm²/10 min at least one ester of a ($C_4$ to $C_6$) alkanol with a $C_{16}$ to $C_{20}$ fatty acid, particularly hexyl laurate.

The cosmetic agent ma include a liquid oil with a spreadability value (25° C.) in a range of 100 mm²/10 min to less than 800 mm²/10 min in a total amount of 32 to 42% by weight.

The cosmetic agent may include a liquid oil with a spreadability value (25° C.) in a range of 800 mm²/10 min to less than 1050 mm²/10 min in a total amount of 35 to 50% by weight.

The cosmetic agent may include a liquid oil with a spreadability value (25° C.) in a range of 1050 mm²/10 min to 1800 mm²/10 min in a total amount of 12 to 22% by weight.

The total amount of the oils named under (b) relative to the sum of the respective total amounts of the oils named under (a) and (c) may be in the range of 1.5 to 1 to 1 to 2, particularly preferably between 1.2 to 1 and 1 to 1.8, and very particularly preferably between 1 to 1.2 to 1 to 1.7.

The cosmetic agent may also include at least one fatty acid ester of at least one linear or branched $C_6$ to $C_{18}$ fatty acid with ascorbic acid.

The cosmetic agent may also include a carotenoid, particularly β-carotene.

The cosmetic agent may also be transparent, and may also include 2,2-dimethyl-6-hydroxy-7-methoxychroman.

The cosmetic agent may include 0 to 0.1% by weight of free water.

The cosmetic agent may be used as a skin cosmetic and further may be used to protect the skin from drying out.

A method includes applying the above-described cosmetic agent to the skin and leaving the agent on the skin, particularly for at least one hour.

EXAMPLES

The following cosmetic agent according to invention was prepared:

TABLE 1

Skin care oils

| Ingredient | Spreadability value [mm²/10 min] | E1 [% by weight] | E2 [% by weight] | E3 [% by weight] |
|---|---|---|---|---|
| Dicaprylyl carbonate | 1611 | 15.00 | 15.00 | 15.00 |
| Hexyl laurate | 1108 | 5.00 | 5.00 | 5.00 |
| Isopropyl stearate | 1004 | To 100 | To 100 | To 100 |
| 2-Ethylhexyl palmitate | 904 | 20.00 | 20.00 | 20.00 |
| C12-15 Alkyl benzoate | 738 | 4.80 | 5.00 | 5.00 |
| 2-Octyldodecanol | 605 | 30.00 | 30.00 | 30.00 |
| Caprylic/capric triglyceride | 552 | 1.90 | 1.90 | 1.90 |
| Almond oil | 201 | — | 4.00 | — |
| Tocopheryl acetate | | 0.50 | — | — |
| Ascorbyl tetraisopalmitate | | 0.50 | 0.50 | — |
| Palmitoyl tripeptide-38 | | 0.0001 | 0.0001 | 0.0001 |
| Dimethylmethoxy chromanol | | 0.01 | 0.01 | 0.01 |
| Tocopherol | | 0.05 | 0.05 | 0.05 |
| β-Carotene | | 0.0002 | 0.0002 | 0.0002 |
| Water | | 0.001 | 0.001 | — |
| Perfume | | 0.40 | 0.75 | 0.40 |
| Ratio of (a) to (b) + (c) | | 1 to 1.68 | 1 to 1.41 | 1 to 1.70 |
| Ratio of (b) to (a) + (c) | | 1 to 1.36 | 1 to 1.61 | 1 to 1.33 |

All oils were mixed together and stirred at room temperature. Then the additives such as active substances, colorant, and perfume oil were added and stirred also at room temperature until it was homogeneous.

Transparent oils were obtained in each case, which were storage-stable.

The spreadability values were determined at 25° C. according to method in the patent description.

A dermatological application test was conducted in 50 subjects with Formulation E1 from Table 1. The subjects used Formulation E1 for a period of 4 weeks in each case in the morning and evening to care for the facial skin. The subjects were questioned at the end.

All subjects confirmed a good to very good skin tolerance.

Further, the following effects were confirmed by the subjects:

90% confirmed a good distribution on the skin.
74% confirm a good to very good absorption of the oil.
76% confirmed a good to very good skin feel.
84% confirmed that the skin did not feel sticky or oily.
86% confirmed that the skin felt smooth and velvety.
86% confirmed that the skin felt velvety-satiny.
78% confirm that the skin is supplied well to very well with moisture.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic agent including, based in each case on the total weight of the agent, liquid oils in a total amount of 80 to 99.5% by weight, wherein the liquid oils include
   (a) at least one liquid oil with a spreadability value (25° C.) in a range of 100 mm²/10 min to less than 800 mm²/10 min,
   (b) at least one liquid oil with a spreadability value (25° C.) in a range of 800 mm²/10 min to less than 1050 mm²/10 min, and
   (c) at least one liquid oil with a spreadability value (25° C.) in a range of 1050 mm²/10 min to 1800 mm²/10 min,
   with the proviso that the weight ratio of the total amount of the oils named under (a) to the sum of the respective total amounts of the oils named under (b) and (c) is in the range of 1 to 3 to 1 to 1.

2. The cosmetic agent according to claim 1, wherein the liquid oil with a spreadability value (25° C.) in a range of 100 mm²/10 min to less than 800 mm²/10 min includes at least one liquid compound of the general formula (I)

wherein $R^1$ is a $C_2$ to $C_{10}$ hydrocarbon group, and $R^2$ is a $C_4$ to $C_{12}$ hydrocarbon group.

3. The cosmetic agent according to claim 1, wherein the liquid oil with a spreadability value (25° C.) in a range of 100 mm²/10 min to less than 800 mm²/10 min includes at least one liquid compound of the general formula (II)

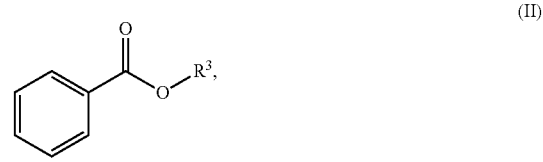

wherein $R^3$ stands for a $C_{10}$ to $C_{16}$ hydrocarbon group.

4. The cosmetic agent according to claim 1, wherein the liquid oil with a spreadability value (25° C.) in a range of 800 mm²/10min to 1050 mm²/10 min includes at least one compound of the formula (III)

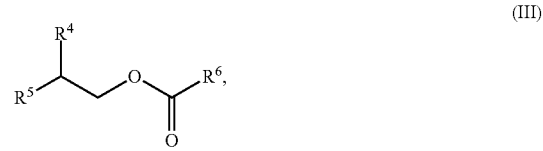

wherein $R^4$ is an alkyl group haveing 2 to 4 carbon atoms, $R^5$ is an alkyl group having 4 to 6 carbon atoms, and $R^6$ is an alkyl group having 7 to 17 carbon atoms.

5. The cosmetic agent according to claim 1, wherein the liquid oil with a spreadability value (25° C.) in a range of 800 mm²/10 min to less than 1050 mm²/10 min includes at least one ester of isopropanol with a $C_{16}$ to $C_{20}$ fatty acid.

6. The cosmetic agent according to claim 1, wherein the liquid oil with a spreadability value (25° C.) in a range of 1050 mm²/10 min to 1800 mm²/10 min includes at least one compound of the formula (IV)

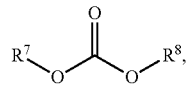
(IV)

wherein $R^7$ and $R^8$ independently of one another are a linear or branched alkyl group having 6 to 10 carbon atoms.

7. The cosmetic agent according to claim 1, wherein the liquid oil with a spreadability value (25° C.) in a range of 1050 mm²/10 min to 1800 mm²/10 min includes at least one ester of a ($C_4$ to $C_6$) alkanol with a $C_{16}$ to $C_{20}$ fatty acid.

8. The cosmetic agent according to claim 1, wherein the liquid oil with a spreadability value (25° C.) in a range of 100 mm²/10 min to less than 800 mm²/10 min is includes in a total amount of 32 to 42% by weight.

9. The cosmetic agent according to claim 1, wherein the liquid oil with a spreadability value (25° C.) in a range of 800 mm²/10 min to less than 1050 mm²/10 min is included in a total amount of 35 to 50% by weight.

10. The cosmetic agent according to claim 1, wherein the liquid oil with a spreadability value (25° C.) in a range of 1050 mm²/10 min to 1800 mm²/10 min is included in a total amount of 12 to 22% by weight.

* * * * *